US011083875B2

(12) United States Patent
McDonald

(10) Patent No.: US 11,083,875 B2
(45) Date of Patent: Aug. 10, 2021

(54) HYBRID MICROCATHETER GUIDEWIRE

(71) Applicant: Michael B. McDonald, Cordova, TN (US)

(72) Inventor: Michael B. McDonald, Cordova, TN (US)

( * ) Notice: Subject to any disclaimer, the term of this patent is extended or adjusted under 35 U.S.C. 154(b) by 471 days.

(21) Appl. No.: 15/890,767

(22) Filed: Feb. 7, 2018

(65) Prior Publication Data

US 2018/0161549 A1   Jun. 14, 2018

Related U.S. Application Data

(63) Continuation-in-part of application No. 15/602,463, filed on May 23, 2017, now Pat. No. 10,898,682, which is a continuation-in-part of application No. 15/445,272, filed on Feb. 28, 2017, now Pat. No. 10,898,322.

(60) Provisional application No. 62/340,111, filed on May 23, 2016, provisional application No. 62/301,270, filed on Feb. 29, 2016.

(51) Int. Cl.
*A61M 25/01* (2006.01)
*A61M 25/09* (2006.01)
*A61M 25/00* (2006.01)
*A61F 2/24* (2006.01)

(52) U.S. Cl.
CPC .. *A61M 25/09041* (2013.01); *A61M 25/0012* (2013.01); *A61M 25/0015* (2013.01); *A61M 25/0023* (2013.01); *A61M 25/0054* (2013.01); *A61M 25/0102* (2013.01); *A61M 25/09025* (2013.01); *A61F 2/2427* (2013.01); *A61M 25/0041* (2013.01); *A61M 2025/0042* (2013.01); *A61M 2025/09075* (2013.01)

(58) Field of Classification Search
CPC ........ A61M 25/09041; A61M 25/0012; A61M 25/0015; A61M 25/0023; A61M 25/0054; A61M 25/0102; A61M 25/09025
USPC ....................................................... 600/585
See application file for complete search history.

(56) References Cited

U.S. PATENT DOCUMENTS

| | | | | |
|---|---|---|---|---|
| 4,003,369 A * | 1/1977 | Heilman | ............... | A61M 25/09 600/585 |
| 4,854,330 A * | 8/1989 | Evans, III | ............. | A61M 25/09 600/585 |
| 5,833,706 A * | 11/1998 | St. Germain | ....... | A61M 25/104 606/194 |
| 6,841,214 B1 * | 1/2005 | Keith | ................... | B29D 23/001 428/35.8 |

(Continued)

*Primary Examiner* — Daniel L Cerioni
(74) *Attorney, Agent, or Firm* — Angela Holt; Bradley Arant Boult Cummings LLP

(57) ABSTRACT

A microtube guide has a microtube combined with a free-floating and removable core. The microtube is generally hollow with a tube shaft and a distal ring, the tube shaft and the distal ring formed from flexible plastic. The distal ring is conformable to the core and straightenable for insertion into a patient's body, and deploys when the core is withdrawn to form a loop. The core is received by the microtube and is configured to advance into the distal ring to cause a diameter of the distal ring to expand, retract, or straighten. The core comprises a tapered segment that tapers in outer diameter from the diameter of the main core wire to a smaller diameter. A distal end segment of microtubing is frictionally affixed to the tapered segment.

17 Claims, 6 Drawing Sheets

(56) References Cited

U.S. PATENT DOCUMENTS

| | | | |
|---|---|---|---|
| 2005/0216053 A1* | 9/2005 | Douk | A61F 2/013 606/200 |
| 2008/0228209 A1* | 9/2008 | DeMello | A61B 17/32056 606/159 |
| 2009/0275862 A1* | 11/2009 | Elsesser | A61M 25/09 600/585 |
| 2010/0256528 A1* | 10/2010 | Lippert | A61B 18/1492 600/585 |
| 2014/0155994 A1* | 6/2014 | McDonald | A61F 2/2496 623/2.11 |
| 2016/0001045 A1* | 1/2016 | Haarer | A61M 25/0662 604/164.1 |

* cited by examiner

HYBRID MICROCATHETER GUIDEWIRE

REFERENCE TO RELATED APPLICATIONS

This application is a continuation-in-part of, and claims priority to, U.S. Non-provisional application Ser. No. 15/602,463, entitled "Microtube Guide," and filed on May 23, 2017, which claims priority to Provisional Patent Application U.S. Ser. No. 62/340,111, entitled "Microtube Guide" and filed on May 23, 2016, which is fully incorporated herein by reference. U.S. Non-provisional application Ser. No. 15/602,463 is a continuation-in-part of, and claims priority to, U.S. Non-provisional application Ser. No. 15/445,272, entitled "TAVR Valve Guidewire and Guidetube with Adjustable Distal Loop," and filed on Feb. 28, 2017, which claims priority to U.S. Provisional Patent Application Ser. No. 62/301,270, entitled "TAVR Valve Guidewire and Guidetube with Adjustable Distal Loop" and filed on Feb. 29, 2016. These patent applications are fully incorporated herein by reference.

BACKGROUND AND SUMMARY

Guidewires, tiny wires designed to navigate vessels within the body, are used in a vast array of medical procedures. After a guidewire is advanced to its desired treatment site, the guidewire acts as a guide that larger catheters can rapidly follow for advancement to the treatment site.

Often in cardiovascular procedures, multiple different types of guidewires are required to perform the desired task. The guidewires are used to navigate medical devices such as catheters and other medical devices in and out of vascular areas and other body regions. The end location and the specific medical device determines what type of guidewire is best suited for the task. The present transcatheter aortic valve replacement (TAVR) procedure requires the exchange of guidewires 6 to 7 times during the course of the operation. With this new hybrid device, the guidewire exchange during the TAVR procedure can be reduced to two exchanges in most cases. This change in procedure will result in a significant reduction in operating time and some savings in material costs. The reduction in operating time should have a positive safety effect and a substantial cost savings result.

The unique construction of the device according to the present disclosure allows it to act as multiple different types of guidewires all in one device. Most currently-used guidewires are constructed of a solid wire or fixed core or slightly-movable core wrapped with wire. These wires have a set flexural strength (flexural modulus) that may vary in different segments of the wire, but the flexural strength at any one segment of the guidewire cannot be changed or adjusted after manufacture or during use in a patient.

A microtube guide according to the present disclosure is a unique "hybrid" concept that uses a microcatheter as the outer component of the guide and a free and movable central core as the inner component of the guide. The distal end of the microcatheter is closed, not open as in a typical catheter. The design of the distal end may vary as needed for different vascular procedures.

The central core of the microtube guide may be tapered for a portion of its distal end, and by adjusting the depth of core insertion into the microcatheter, the stiffness of that segment of the guide may be adjusted. The depth of core insertion or retraction can also be used to change the configuration of the microcatheter guide.

Because the central core drives the stiffness of the guide, cores can be exchanged for other cores having different stiffness, distal taper, or even core wire shape—all with the same outer tube (microcatheter). The core exchange can even be done during the procedure while the outer component of the guide is in the patient. The guide of the present disclosure thus provides the capability of changing wire support during a procedure without having to exchange the device.

Being able to adjust the depth of the unique core can change the configuration of the microtube guide. The shape of the distal end of the central core can be formed as desired by the thermoset process of the polyimide or other manufacturing processes. Advancing or retracting the core can vary this shape of the distal end. Exchanging the core for a stiff or softer, long taper or short taper, distal end can also change the guide's distal configuration or transport performance of the desired device.

In addition, having the outer surface of the device being a smooth microcatheter construction and not a wire wrapped core (as are most of our present guidewires) is be less traumatic to the human tissues. In use with heart TAVR procedures, this characteristic should help prevent wire perforations of the heart or other cardiac or vascular damage.

In some embodiments, these "hybrid" devices will be constructed of a polyimide (or similar substance) microcatheter with or without braid as an internal component. Unlike currently-used microcatheters, the distal end will not be open to the patient. The size (OD) will vary upon the device application—coronary, peripheral, structural heart, cerebral, etc. The inner core is a PTFE coated stainless steel wire or nitinol in one embodiment.

Adjustment collars of the microtube may be used to hold the core position within the microtube, as discussed herein.

DETAILED DESCRIPTION

Figure 1:
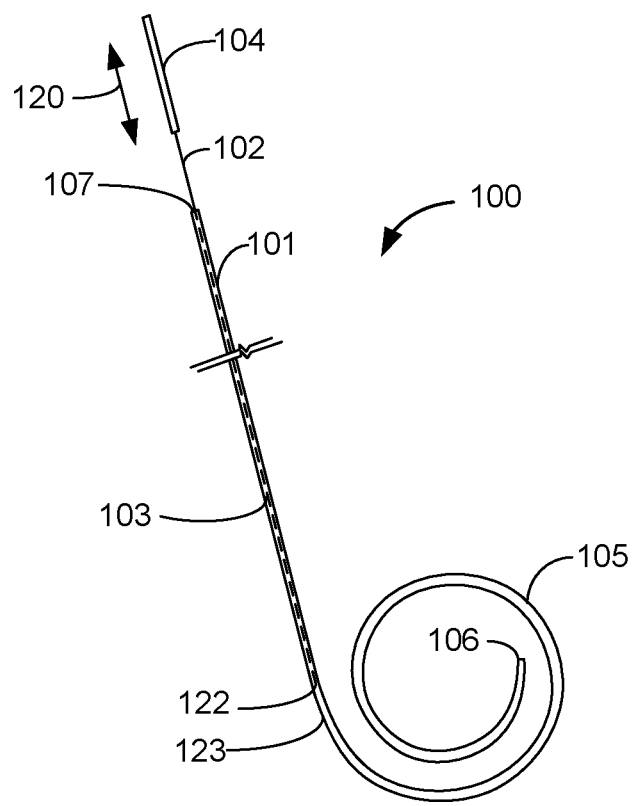
FIG. 1 depicts a microcatheter guide according to an exemplary embodiment of the present disclosure.

FIG. 1 depicts a microtube guide 100 comprising a microtube 101 combined with a free-floating and removable core 102 according to the present disclosure. The microtube 101 is a hollow microcatheter, formed from plastic in one embodiment. A proximal opening 107 of the microtube 101 receives the core 102, which slides within the microtube 101 to advance and retract in the direction indicated by directional arrow 120.

The microtube 101 comprises a generally straight main shaft 103 that is hollow to receive the core 102. The microtube 101 further comprises an expandable distal loop 105. The distal loop 105 is disposed at a distal end 106 of the microtube 101. The distal end 106 of the microtube is closed in the illustrated embodiment, and not open like typical microcatheters.

Figure 2:
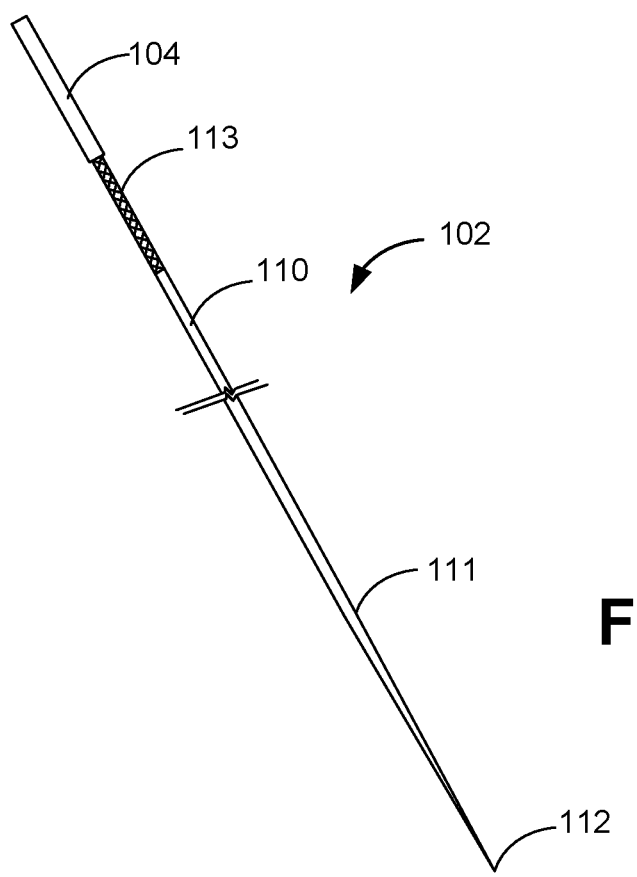
FIG. 2 depicts an exemplary core of the microcatheter guide according to an embodiment of the present disclosure.

The guide further comprises a proximal core end 104, which in the illustrated embodiment is a section of microcatheter tubing that is fixed to the core 102. The outer diameter of the proximal end is generally the same as the outer diameter of the microtube 101. When the guide is initially being fed into a patient's vessels, the core 102 may be fully advanced within the microtube 101, i.e., such that there is not an exposed section of core 102 as is shown in FIG. 2. The proximal core end 104 being formed from microcatheter tubing of the same diameter as the microtube 101 provides a smooth, gap-free (or minimal gap) outer surface of the guide 100 when the guide is being fed into the patient.

The main shaft 103 of the microtube 101 is formed from kink-resistant, thin-walled, semi-rigid plastic tube that is 0.035 inches in outer diameter and 0.028 inches in inner diameter in one embodiment. In other embodiments, the main shaft 103 is formed with braided steel within the plastic of the guidetube (polyimide braid, for example).

In one embodiment, the distal loop 105 is slightly larger in cross-sectional diameter than the main shaft 103, and formed from kink-resistant, semi-rigid plastic tubing that is the range of 0.045-0.054 inches in outer diameter. A transition portion (not shown) between the main shaft 103 and the distal loop 105 transitions the main shaft 103 to the distal loop 105 in one embodiment. In this regard, the main shaft 103 may be fused to the distal loop 105 at the transition portion.

The distal loop 105 being larger in diameter than the main shaft 103 helps to prevent excessive forward advancement of the valve delivery system (not shown) that delivers the replacement valve. In addition, the distal loop 105 being larger in diameter may simplify forming of the microtube 101. In this regard, the main shaft 103 may be fit within and be frictionally received by the distal loop 105 prior to fusing of the main shaft 103 to the distal loop 105.

The distal loop 105 is softer than the main shaft 103, and when not acted upon by an external catheter (not shown) or the core 102, the distal loop forms a loop as shown. In the illustrated embodiment, the body of the distal loop makes about one and one half loops. An outer diameter of the distal loop in this configuration may be about 3.0 centimeters.

When the core 102 is advanced such that its tip 122 (shown in dashed line) enters the distal loop 105, the tip 122 contacts an inner surface 123 of the distal loop 105 and causes the diameter of the distal loop 105 to increase. By advancing or retracting the core 102, the size of the distal loop 105 may be enlarged or decreased. Further, the distal loop 105 may fully straighten upon advancement of the core 102 as well.

Although FIG. 1 illustrates a distal loop 105 that extends downwardly from the guide, in other embodiments, the loop may be disposed horizontally to the microtube 101, i.e., perpendicular to the microtube 101, or otherwise oriented differently.

FIG. 2 depicts an enlarged view of an exemplary core 102 according to an embodiment of the present disclosure. The core 102 is advanced through the proximal opening 107 (FIG. 1) of the microtube 101.

The core 102 comprises a main shaft 110 and a tapered distal end 111. The main shaft 110 and the distal end 111 are formed from flexible polytetrafluoroethylene (PTFE) coated stainless steel in one embodiment. In this embodiment, the distal end 111 is smaller in diameter than the main shaft 110 and tapers from the diameter of the main shaft 110 to a distal tip 112. The distal tip 112 is received by the proximal opening 107 (FIG. 1) of the microtube 101 (FIG. 1) and advances into the distal loop 105 (FIG. 1) of the microtube 101.

As discussed above with respect to FIG. 1, the core 102 further comprises a proximal core end 104 that is a section of microcatheter tubing fixed to the main shaft 110 of the core 102. An adjustment section 113 of the core 102 is disposed adjacent to the proximal core end 104. In the illustrated embodiment, the adjustment section 113 is shown as textured (e.g., etched). The texture in the adjustment section may help the core 102 grip the inside of the microtube 101 (FIG. 1).

Figures 3, 4:
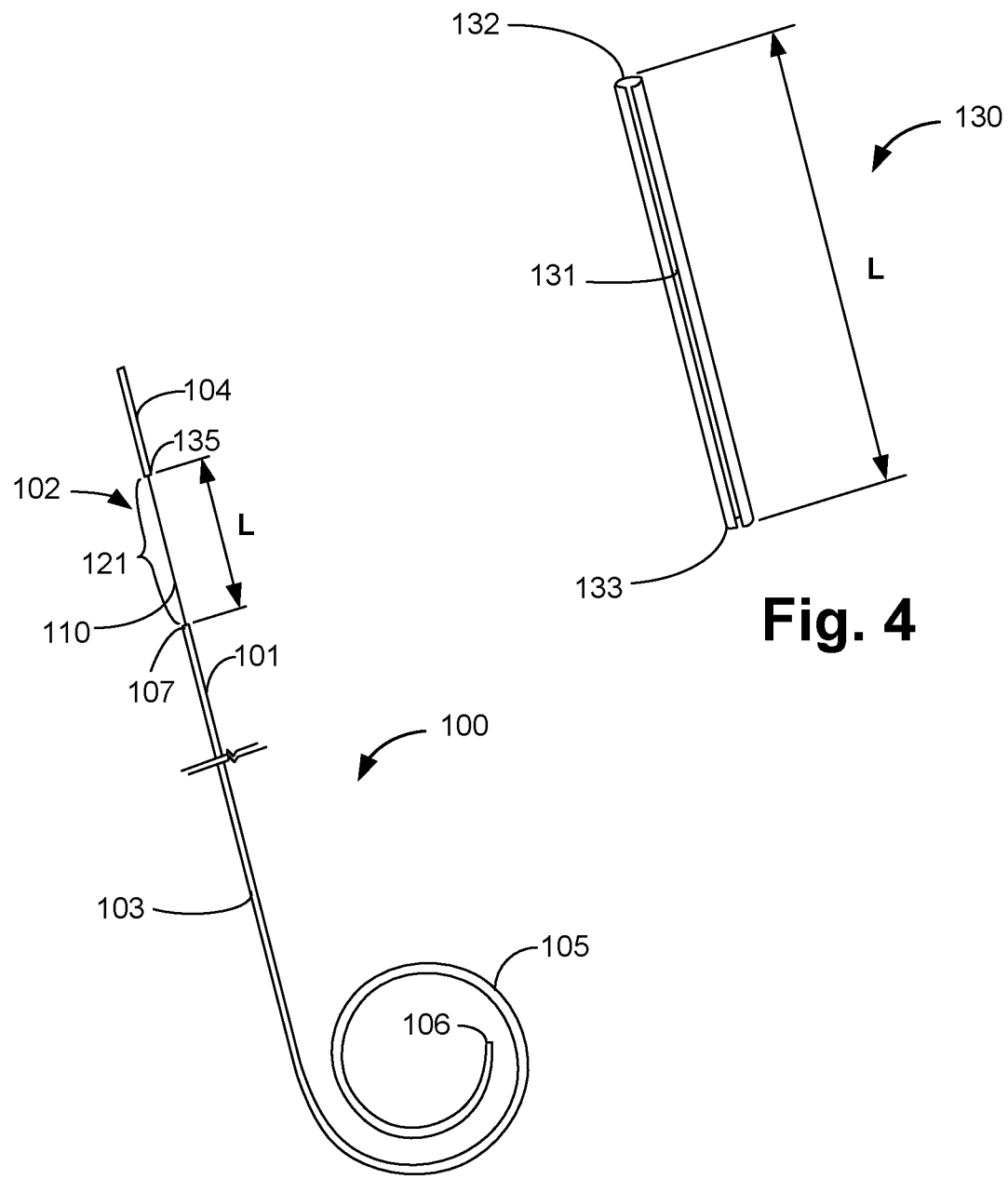
FIG. 3 depicts the guide of FIG. 1, showing the adjustment capability of the guide.
FIG. 4 depicts an exemplary adjustment collar for adjusting the guide.

FIG. 3 depicts the guide 100 of FIG. 1, showing an exposed section 121 of the main shaft 110 of the core 102 between the microtube 101 and the proximal core end 104 of the guide 100. The proximal core end 104 is fixed to the main shaft 110 of the core 102, and the core 102 is received by and slides within the microtube 101. In a method for operating the guide 100, the user (not shown) advances the core 102 within the microtube 101 until the core 102 expands the distal loop 105 to the desired diameter. When the core 102 has been advanced as desired, the exposed section 121 of core 102 will be a length "L" as indicated in FIG. 3. At this point, a collar 130 (FIG. 4) of the same length "L" may be placed onto the exposed section 121, fitting over the core 102 between a lower end 135 of the proximal core end 104 and the proximal opening 107. The collar 130 serves to fix the core 102 within the microtube 101 such that it cannot advance further into the microtube 101.

FIG. 4 depicts an enlarged view of an exemplary collar 130 as discussed above with respect to FIG. 3. The collar 130 comprises a generally semi-cylindrical ("C"-shaped) section of microtubing of a length "L," with a slit 131 that is sized so that the collar 130 can fit over the main shaft 110 (FIG. 3) of the core 102 (FIG. 3). The collar 130 further comprises a proximal collar end 132 and a distal collar end 133. When the collar 130 is installed on the guide 100 (FIG. 3), the proximal collar end 132 is adjacent to and contacts the lower end 135 (FIG. 3) of the proximal core end 104 (FIG. 3), and the distal collar end 133 is adjacent to and contacts the proximal opening 107 (FIG. 3) of the microtube 101 (FIG. 3). The collar 130 may be any of various lengths "L," which lengths are determined by the lengths desired for the user to get the desired advancement of the core 102 within the microtube 101. Thus multiple collar lengths are available depending on the length desired by the user.

Figure 5:
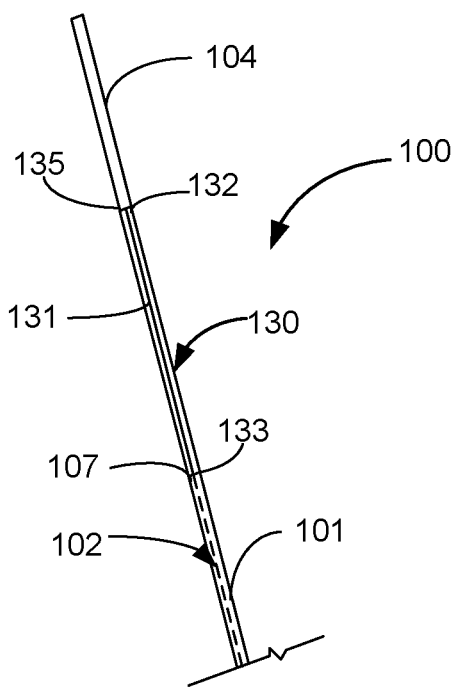
FIG. 5 depicts a partial view of the guide showing an adjustment collar installed over the core to set the distance the core is advanced within the microtube.

FIG. 5 depicts a partial view of the guide 100 with the collar 130 installed on the guide 100 to temporarily fix the length of the core 102 (shown in dashed line) that is advanced within the microtube 101. The collar 130 has an outer diameter that is generally the same as the microtube 101 and the proximal core end 104 of the core 120, such that when the collar 130 is installed, the outer surfaces of the proximal core end 104, the collar 130, and the microtube 101 are generally flush.

In an exemplary operation of the guide 100, the core 102 may initially be fully advanced into the microtube 101 such that the microtube 101 is generally straight, with no looped distal end. In this configuration, the lower end 135 of the proximal core end 104 is adjacent to and contacts the proximal opening 107 of the microtube 101. Two users (not shown) may be required to hold the guide 100 during installation and use due to the length of the guide 100. One user typically holds the proximal core end 104 of the core 102 while the other user maneuvers the distal end of the guide 100 into the patient. When the guide 102 is used in a TAVR procedure, for example, after the distal end of the microtube 101 crosses the valve, the person holding the proximal core end 104 may hold it steady while the other person advances the microtube 101 slightly to deploy the distal end 105 into a loop as discussed herein. When the distal end 105 is deployed as desired, a collar 130 of the desired length "L" can be installed in the now-exposed space between the lower end 135 of the proximal core end 104 and the proximal opening 107 of the microtube 101.

In other embodiments, the microtube (not shown) may not have a distal ring. Rather, the microtube may conform to a shape and stiffness of a core (not shown) that has some other shape.

Figure 6:
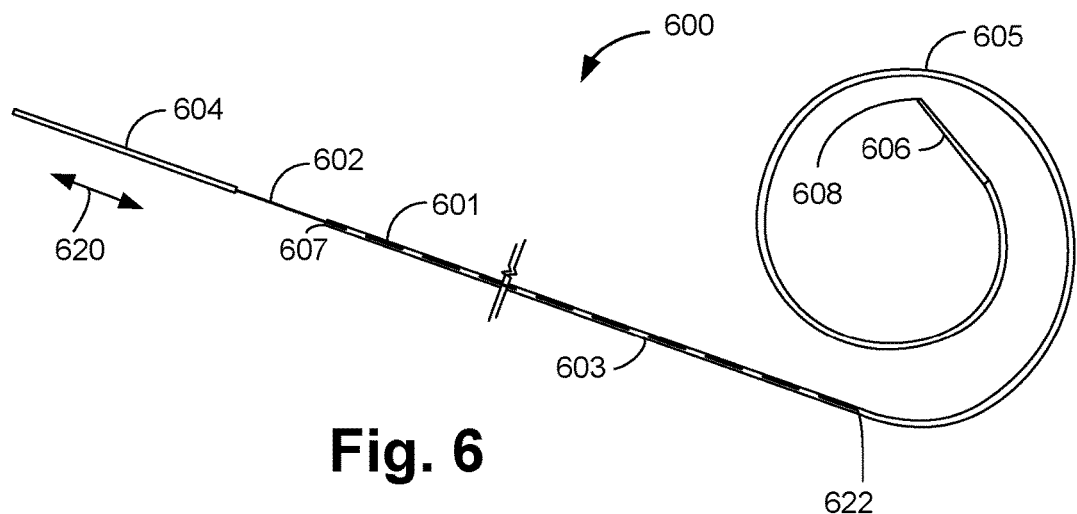
FIG. 6 depicts an alternative embodiment of a microtube guide according to the present disclosure.

FIG. 6 depicts an alternative embodiment of a microtube guide 600 according to the present disclosure. The microtube guide 600 comprises a microtube 601 combined with a free-floating and removable core 602. The microtube 601 is a hollow microcatheter, formed from plastic in one embodiment. Further, in one embodiment, the outer diameter of the microtube 601 is substantially 0.035 inches and the inner diameter of the microtube 601 is 0.028 inches.

A proximal opening 607 of the microtube 601 receives the core 602, which slides within the microtube 601 to advance and retract in the direction indicated by directional arrow 620. In one embodiment, the core 602 has an outer diameter of 0.026 inches, slightly smaller than the inner diameter of the microtube 601, a difference of 0.002 inches from the I.D. of the microtube 601.

The microtube 601 comprises a generally straight main shaft 603 that is hollow to receive the core 602. The dashed line within the microtube 601 represents the core 602 sliding within the microtube 601.

The microtube 601 further comprises an expandable distal loop 605. The distal loop 605 is disposed near a distal end 608 of the microtube 601. Although the distal loop 605 is shown as a loop in FIG. 6, in use on a patient, the distal loop 605 may be looped as shown or substantially straight, as further discussed herein. The distal end 608 of the microtube is closed in the illustrated embodiment, and not open like typical microcatheters.

The guide 600 further comprises a proximal core end 604, which in the illustrated embodiment is a section of microcatheter tubing that is fixed to the core 602. The outer diameter of the proximal end 604 is generally the same as the outer diameter of the microtube 601. When the guide is initially being fed into a patient's vessels, the core 602 may be fully advanced within the microtube 601, i.e., such that there is not an exposed section of core 602 as is shown in FIG. 6. The proximal core end 604 being formed from microcatheter tubing of the same diameter as the microtube 601 provides a smooth, gap-free outer surface of the guide 600 when the guide is being fed into the patient.

The microtubing in the area of the distal loop 605 is softer than that of the main shaft 603, and when not acted upon by an external catheter (not shown) or the core 602, the distal loop forms a loop as shown. In the illustrated embodiment, the body of the distal loop 605 makes about one and one half loops, or approximately 540 degrees. An outer diameter of the distal loop in this configuration may be about 3.0 centimeters.

When the core 602 is advanced such that its tip 622 (shown in dashed line) enters the distal loop 605, the tip 622 contacts an inner surface (not shown) of the distal loop 605 and causes the diameter of the distal loop 605 to increase. By advancing or retracting the core 602, the size of the distal loop 605 may be enlarged or decreased. Further, the distal loop 605 may fully straighten upon advancement of the core 602 as well.

The distal end of the microcatheter is set in at least a 360 degree loop. The diameter of the distal loop is determined by the procedure it is designed for. The distal loop for TAVR will be in the range of 2 to 3 cm in diameter.

A distal tip 606 is disposed at the distal end 608 of the microtube 601. The distal tip 606 is not hollow like the microtube 601, but rather is solid, with no central lumen. The distal tip 606 of the microcatheter's loop 605 is softer than the microtube 601 to be atraumatic and more flexible. The distal tip 606 is between 1.0 cm and 1.5 cm long in one embodiment.

In one embodiment, the microtube 601 is a thermoset polymer that retains its shape and recoil even through multiple tasks and prolonged exposure to body temperature. The device of the illustrated embodiment is constructed of polyimide that is reinforced with a stainless steel braid. The stainless steel braid helps prevent the microcatheter from kinking in tortuous vascular areas. In one embodiment, the polyimide is impregnated with PTFE granules to create a low coefficient of friction.

Figure 7:
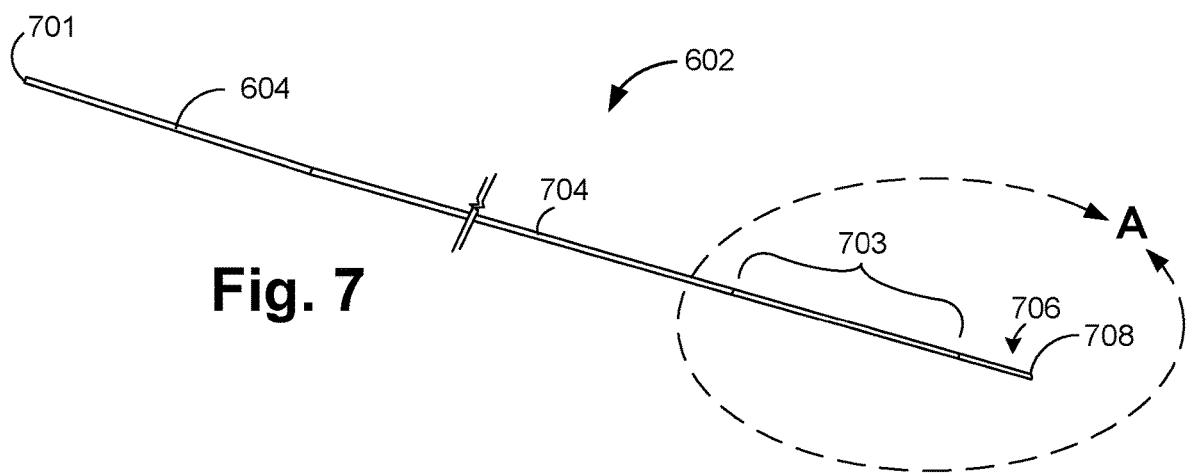
FIG. 7 depicts an exemplary core of the microcatheter guide according to an embodiment of the present disclosure.

FIG. 7 depicts an exemplary embodiment of the core 602 of FIG. 6 removed from the microtube 601. The unique core 602 controls the performance and shape of the microcatheter 600 (FIG. 6). The core 602 can change the configuration of the distal end of the microcatheter 600 from the full loop to a slight curve to substantially straight. The shape control is determined by adjusting the depth of the core 602 in the distal loop 605 (FIG. 6), as further discussed herein.

The main shaft 704 of the core 602 comprises PTFE-coated stainless steel wire 0.026" in outer diameter, in one embodiment. A tapered segment 703 of the core 602 is disposed near a distal end 708 of the core 602. The tapered segment 703 extends between the main shaft 704 and the distal end portion 706, and is shown in further detail in FIG. 7A. The tapered segment 703 is tapered specifically for control of the microcatheter. The tapering allows that area of the guide to be more flexible, by allowing controlled expansion of the distal loop (and support), without completely straightening it.

The distal end segment 706 of the core 602 is disposed at the distal end 708 of the core 602. The distal end segment 706 comprises polyimide with stainless steel braid microcatheter (0.026" outside diameter). In this regard, the very distal end of the core consists of a short segment of microcatheter over the stainless steel wire's tip e.g., slid over the tapered portion 703 and held in place frictionally, in one embodiment.

The distal end segment 706 of the core 602 is constructed of the same material as the larger, outer microcatheter itself, but with an outer diameter just less the inner diameter of the outer microcatheter. The outer diameter of the distal end segment 706 is substantially uniform along its length. The configuration of the distal end segment 706 allows a gradual transition of the inner core wire's force on the outer microcatheter to prevent a kinking point in the outer microcatheter.

The distal end segment 706 also provides a contact area with very low friction for interaction of the microtube 601 (FIG. 6) with the core 602. The low friction is a result of the distal end portion 706 being formed from the same material as the microtube, which is polyimide with PTFE granules in one embodiment.

On a proximal end 701 of the core wire is fixed a segment of microcatheter that is substantially identical to the body of the microcatheter. This segment of microcatheter serves as a control handle for setting the depth of the core wire within the outer microcatheter, as further discussed herein.

Figure 7A:
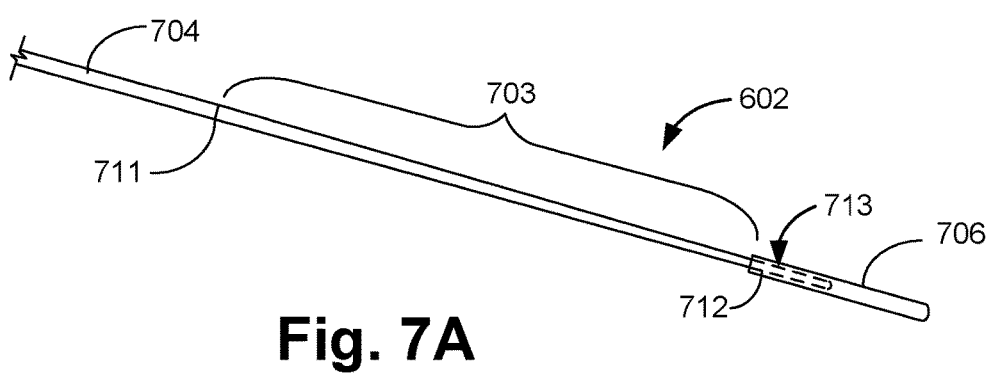
FIG. 7A is an enlarged partial view of the core of FIG. 7, taken along detail line "A" of FIG. 7.

FIG. 7A is an enlarged partial view of the core 602 of FIG. 7, taken along detail line A of FIG. 7. The tapered segment 703 tapers from about 0.026 in outer diameter at its proximal end 711 to about 0.013 inches in outer diameter at its distal end 712, over a distance of about 2.5 cm, in one embodiment.

The distal end segment 706 is frictionally fit over the tapered segment 703 in the illustrated embodiment. In this regard, the inner diameter of the distal end segment 706 is only slightly larger than the outer diameter of the distal end 712 of the tapered segment 703. In one embodiment, the inner diameter of the distal end segment 706 is 0.018" and its outer diameter is 0.026". The distal end segment 706 can therefore slide over the tapered segment 703 (which has an O.D. of 0.013 inches at its distal end) until it stops. As shown in FIG. 7A, there is an overlap portion 713 of the core 602 where the distal end 712 of the tapered segment 703 is within the distal end segment 706, shown in dashed lines in the figure. In one embodiment, the distal end segment 706 is about 1 cm long.

The taper of the tapered segment 703 results in less rigidity of the core 602 at the distal end of the core. Without the gradual tapering of the tapered segment, the distal end of the core may be stiff enough that it could fold over the microcatheter. The distal end segment 706 at the very distal end of the core 602 helps to transition the stiffness on the distal end. With this configuration, if the microcatheter is pushed against a wall, it should not fold over and kink on itself. The result is that the distal loop 605 (FIG. 6) gradually and uniformly expands and contracts.

In one embodiment, the tapering of the tapered segment 703 is formed by grinding, such that the main shaft 704 of the ore and the tapered segment 703 are unitary. Further, in one embodiment the distal end of the tapered segment 703 does not have a PTFE coating and is thus not slick, thus allowing it to frictionally adhere to the distal end segment 706. In other embodiments, adhesives may be used to adhere the distal end segment 706 to the tapered segment 703.

Figure 8:
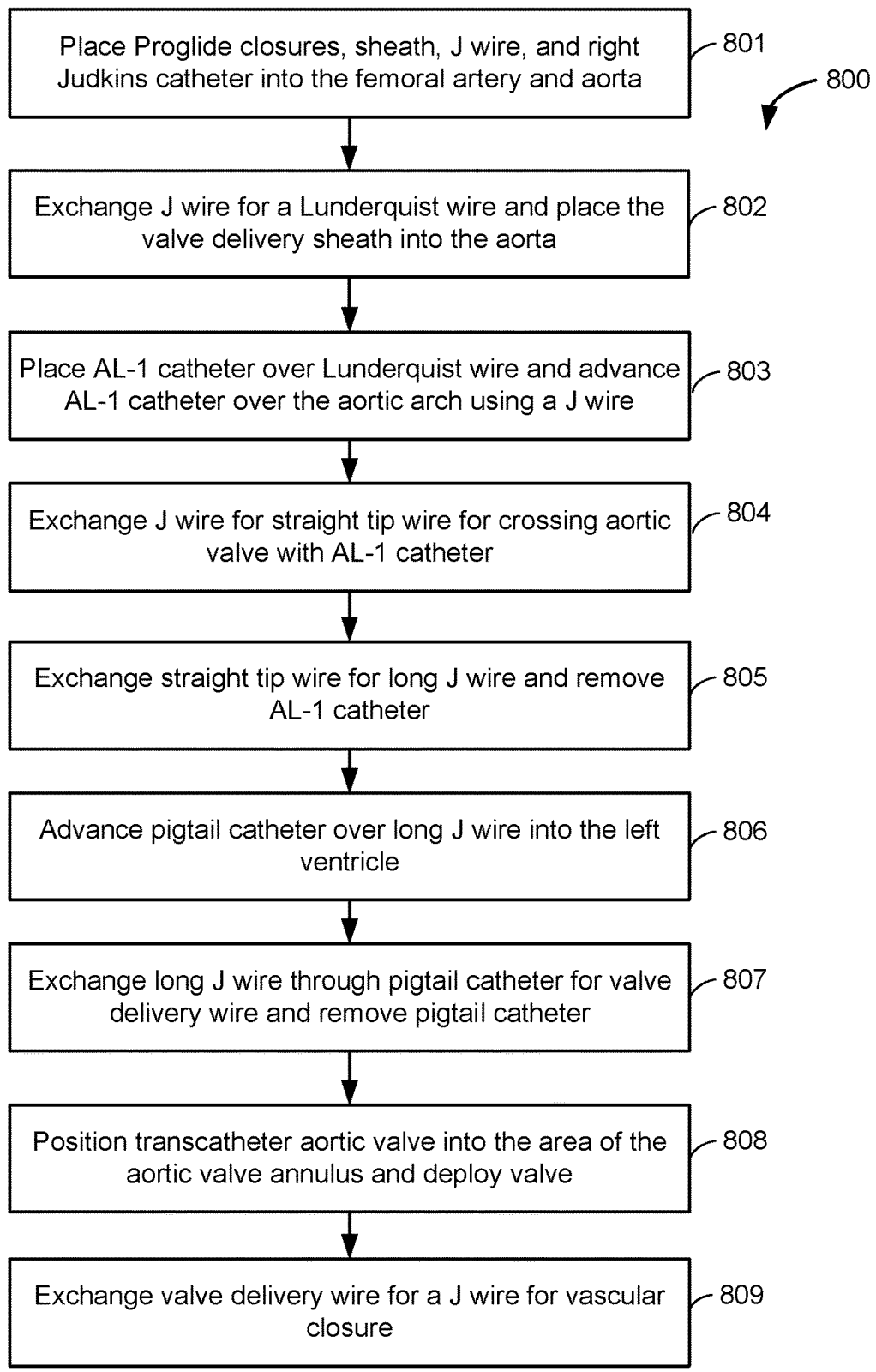
FIG. 8 depicts a prior art method of performing a transcatheter aortic valve replacement.

FIG. 8 depicts a prior art method of performing a transcatheter aortic valve replacement. In step 801, a user places closures (such as Proglide closures), sheath, J wire, and right Judkins catheter into the femoral artery and aorta of a patient. In step 802, the user exchanges the J wire for a Lunderquist wire and places the valve delivery sheath into the aorta.

In step 803, the user places an AL-1 catheter over the Lunderquist wire, and advances the AL-1 catheter over the aortic arch using a J wire. In step 804, the user exchanges the J wire for a straight tip wire for crossing the aortic valve with an AL-1 catheter.

In step 805, the user exchanges the straight tip wire for a long J wire and removes the AL-1 catheter. In step 806, the user advances the pigtail catheter over the long J wire into the left ventricle. In step 807, the user exchanges the long J wire through the pigtail catheter for a valve delivery wire and removes the pigtail catheter.

In step 808, the user positions the transcatheter aortic valve into the area of the aortic valve annulus and deploys the valve. In step 809, the user exchanges the valve delivery wire for a J wire for vascular closure. The valve delivery wire is a relatively large stiff wire and vascular closure cannot be performed over such a wire.

Figure 9:
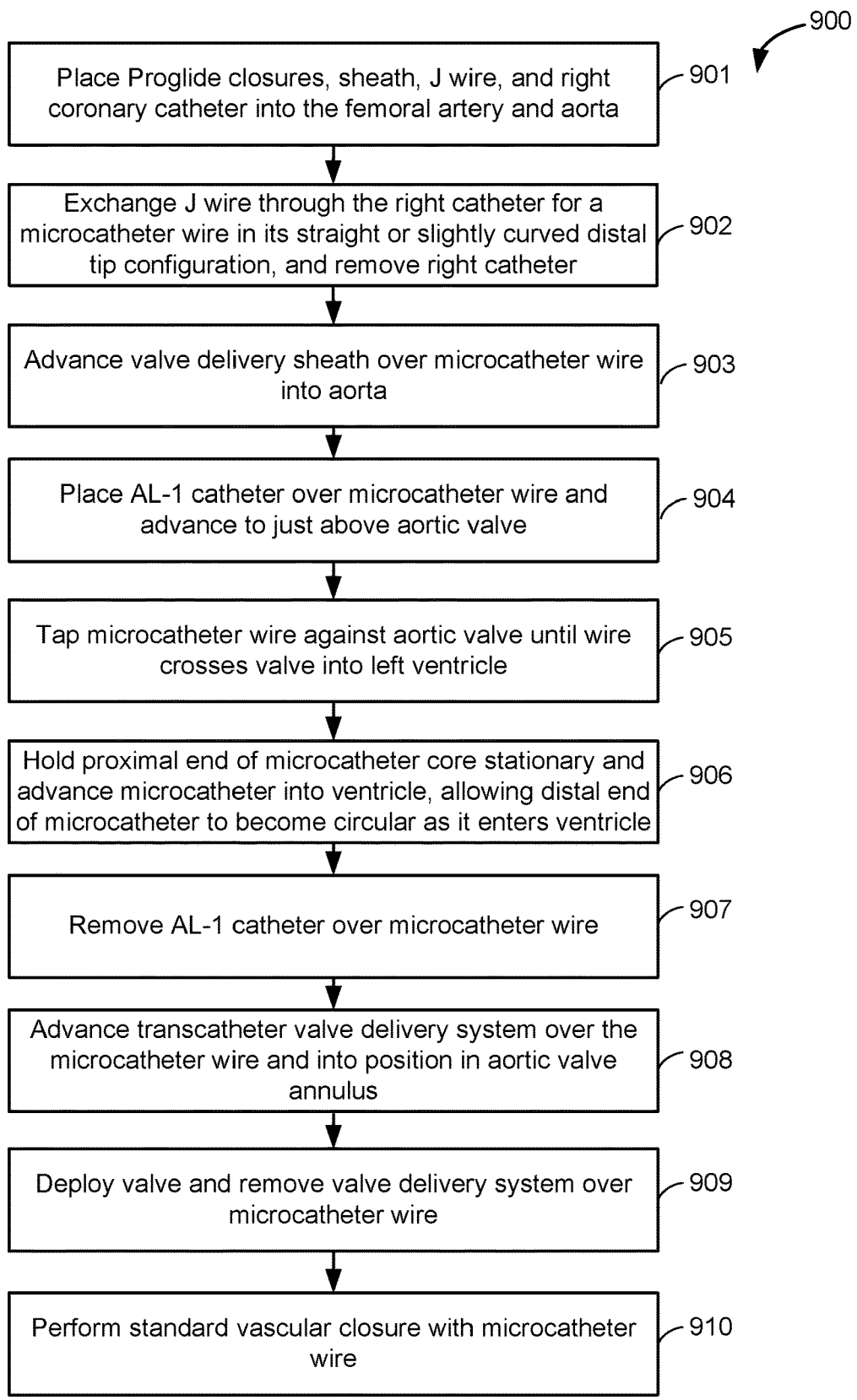
FIG. 9 depicts a method of performing a transcatheter aortic valve replacement using the device disclosed herein according to an exemplary embodiment of the present disclosure.

FIG. 9 depicts a method of performing a transcatheter aortic valve replacement using the device disclosed herein, according to an exemplary embodiment of the present disclosure. In step 901 of the exemplary method, the user places vascular closures (such as Proglide closures), sheath, J wire, and right coronary catheter into the femoral artery and aorta.

In step 902 of the method, the user exchanges the J wire through the right catheter for a microcatheter wire in its straight or slightly curved distal tip configuration, and removes the right catheter.

In step 903 of the method, the user advances the valve delivery sheath over the microcatheter wire into the patient's aorta. In step 904 of the method, the user places an AL-1 catheter over the microcatheter wire and advances it to just above the aortic valve. In step 905 of the method, the user then taps the microcatheter wire against the aortic valve until the wire crosses the valve into the left ventricle.

In step 906, the user holds the proximal end of the microcatheter core stationary and advances the microcatheter into the patient's ventricle, allowing the distal end of the microcatheter to become circular as it enters the ventricle.

In step 907, the user removes the AL-1 catheter over the microcatheter wire. In step 908, the user advances the transcatheter valve delivery system over the microcatheter wire and into position in the aortic valve annulus. In step 909, the user deploys the valve and the removes the valve delivery system over the microcatheter wire.

In step 910, the user performs standard vascular closure with the microcatheter wire. With the device according to the present disclosure, the user can close over the microcatheter/valve delivery wire, by causing the microcatheter wire to become substantially straight. Being able to close over the microcatheter wire results in one less wire exchange in the closure operation.

Further the method 900 results in several fewer wire exchanges than the method 800 of FIG. 8.

The terms "first," "second," and the like are used herein to describe various features or elements, but these features or elements should not be limited by these terms. These terms are used only to distinguish one feature or element from another feature or element. Thus, a first feature or element discussed below could be termed a second feature or element, and similarly, a second feature or element discussed below could be termed a first feature or element without departing from the teachings of the present disclosure. Further, the presence of a "first" or "second" feature or element (or the like) does not imply the presence of any additional such feature or element.

This disclosure may be provided in other specific forms and embodiments without departing from the essential characteristics as described herein. The embodiments described are to be considered in all aspects as illustrative only and not restrictive in any manner.

What is claimed is:

1. A device comprising:
   a generally hollow microtube comprising a tube shaft and a distal ring with a closed distal end, the tube shaft and the distal ring formed from flexible tubing, the tube shaft comprising a proximal opening on a proximal end of the tube shaft, the distal ring forming a downwardly-extending, circular loop when the device is in a deployed configuration, the distal ring formed within a single downwardly-extending plane; and a flexible core receivable by the proximal opening of the tube shaft of the microtube and slideable within the microtube, the core comprising
a proximal core end, the proximal core end comprising a section of microtubing fixed to the core,
a main core shaft,
a tapered segment, the tapered segment tapering in outer diameter from a diameter equal to that of the main core shaft to a smaller diameter,
the microtube and the core configured such that partially advancing the core within the microtube adjusts a shape of the loop of the distal ring, and fully advancing the core within the microtube substantially straightens the microtube.

2. The device of claim 1, wherein an outer diameter of the proximal core end is substantially the same as an outer diameter of the microtube, such that when the core is fully received by the microtube, the device has a consistent outer diameter from the proximal core end to the microtube.

3. The device of claim 1, further comprising a distal end segment affixed to the tapered segment, wherein the distal end segment is constructed of the same material as the microtube, and wherein the distal end segment has an outer diameter slightly less than an inner diameter of the microtube.

4. The device of claim 3, where the tapered segment and distal end segment of the core are configured to advance into the distal ring of the guidetube to increase a diameter of the distal ring without kinking the microtube.

5. The device of claim 1, the core configured to cause the distal ring to straighten when the core is advanced fully into the microtube, the core further configured to cause the distal ring of the microtube to deploy when the core is retracted from the distal ring, the core further configured to cause the diameter of the distal ring to increase when the core is partially advanced into the distal ring.

6. The device of claim 1, wherein the microtube is formed from polyimide with stainless steel braid.

7. The device of claim 6, wherein the polyimide is impregnated with Polytetrafluoroethylene (PTFE) granules, resulting in a low coefficient of friction between the microtube and the core.

8. The device of claim 1, wherein the diameter of the main core shaft is substantially 0.026 inches and the smaller diameter is substantially 0.013 inches.

9. The device of claim 3, wherein the tapered segment has a length of substantially 2.5 centimeters and the distal end segment has a length of substantially 1 centimeter.

10. A device comprising:
a generally hollow microtube comprising a tube shaft and a distal ring with a closed distal end, the tube shaft and the distal ring formed from flexible tubing, the tube shaft comprising a proximal opening on a proximal end of the tube shaft, the distal ring forming a downwardly-extending, circular loop when the device is in a deployed configuration, the distal ring formed within a single downwardly-extending plane; and
a flexible core receivable by the proximal opening of the tube shaft of the microtube and slideable within the microtube, the core comprising
a main core shaft,
a tapered segment, the tapered segment tapering in outer diameter from a diameter equal to that of the main core shaft to a smaller diameter,
a distal end segment affixed to the tapered segment,
the microtube and the core configured such that partially advancing the core within the microtube adjusts a shape of the loop of the distal ring, and fully advancing the core within the microtube substantially straightens the microtube.

11. The device of claim 10, the core further comprising a proximal core end, the proximal core end comprising a section of microtubing fixed to the core.

12. The device of claim 11 wherein an outer diameter of the proximal core end is substantially the same as an outer diameter of the microtube, such that when the core is fully received by the microtube, the device has a consistent outer diameter from the proximal core end to the microtube.

13. The device of claim 10, wherein the distal end segment is constructed of the same material as the microtube, and wherein the distal end segment has an outer diameter slightly less than an inner diameter of the microtube.

14. The device of claim 10, where the tapered segment and distal end segment of the core are configured to advance into the distal ring of the guidetube to increase a diameter of the distal ring without kinking the microtube.

15. The device of claim 10, the core configured to cause the distal ring to straighten when the core is advanced fully into the microtube, the core further configured to cause the distal ring of the microtube to deploy when the core is retracted from the distal ring, the core further configured to cause the diameter of the distal ring to increase when the core is partially advanced into the distal ring.

16. The device of claim 10, wherein the microtube is formed from polyimide with stainless steel braid.

17. The device of claim 16, wherein the polyimide is impregnated with Polytetrafluoroethylene (PTFE) granules, resulting in a low coefficient of friction between the microtube and the core.

* * * * *